United States Patent
Nabeta

(10) Patent No.: US 11,213,486 B2
(45) Date of Patent: *Jan. 4, 2022

(54) DRUG-CONTAINING FAT EMULSION AND METHOD FOR PRODUCING SAME

(71) Applicant: Techno Guard Co. Ltd., Kawasaki (JP)

(72) Inventor: Kiichiro Nabeta, Kawasaki (JP)

(73) Assignee: TECHNO GUARD CO. LTD., Kawasaki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/313,607

(22) PCT Filed: Jan. 10, 2018

(86) PCT No.: PCT/JP2018/000383
§ 371 (c)(1),
(2) Date: Jan. 8, 2019

(87) PCT Pub. No.: WO2018/131620
PCT Pub. Date: Jul. 19, 2018

(65) Prior Publication Data
US 2019/0160008 A1    May 30, 2019

(30) Foreign Application Priority Data

Jan. 12, 2017  (JP) ............... JP2017-003273
Apr. 20, 2017  (JP) ............... JP2017-084052

(51) Int. Cl.
| A61K 9/107 | (2006.01) |
| A61K 47/46 | (2006.01) |
| A61K 47/10 | (2017.01) |
| A61K 47/32 | (2006.01) |
| A61K 31/573 | (2006.01) |
| A61K 47/18 | (2017.01) |
| A61K 47/44 | (2017.01) |
| A61K 47/12 | (2006.01) |
| A61K 47/26 | (2006.01) |
| A61K 47/38 | (2006.01) |
| A61K 47/36 | (2006.01) |
| A61K 47/14 | (2017.01) |
| A61K 47/24 | (2006.01) |
| A61K 9/00 | (2006.01) |
| A61K 47/34 | (2017.01) |

(52) U.S. Cl.
CPC ............ *A61K 9/1075* (2013.01); *A61K 9/007* (2013.01); *A61K 9/0019* (2013.01); *A61K 9/0043* (2013.01); *A61K 9/0046* (2013.01); *A61K 9/0048* (2013.01); *A61K 9/107* (2013.01); *A61K 31/573* (2013.01); *A61K 47/10* (2013.01); *A61K 47/12* (2013.01); *A61K 47/14* (2013.01); *A61K 47/18* (2013.01); *A61K 47/24* (2013.01); *A61K 47/26* (2013.01); *A61K 47/32* (2013.01); *A61K 47/34* (2013.01); *A61K 47/36* (2013.01); *A61K 47/38* (2013.01); *A61K 47/44* (2013.01); *A61K 47/46* (2013.01)

(58) Field of Classification Search
CPC .. A61K 9/1075; A61K 9/0048; A61K 9/0043; A61K 9/0046; A61K 47/34; A61K 9/007; A61K 9/0019; A61K 47/24; A61K 47/14; A61K 9/107; A61K 47/36; A61K 47/38; A61K 47/26; A61K 47/12; A61K 47/44; A61K 47/18; A61K 31/573; A61K 47/32; A61K 47/10; A61K 47/46; A61K 31/405; A61K 31/355; A61K 38/13; A61K 31/436
See application file for complete search history.

(56) References Cited

U.S. PATENT DOCUMENTS

| 7,226,932 B2 * | 6/2007 | Gokhale | ............ A61K 9/1075 424/450 |
| 2012/0121670 A1 * | 5/2012 | Lopez | ............ C12N 15/88 424/401 |

FOREIGN PATENT DOCUMENTS

| CN | 1292689 A | 4/2001 |
| JP | H03-176425 A | 7/1991 |
| JP | 2010270023 | * 12/2010 |
| WO | 98/37869 A1 | 9/1998 |
| WO | 2009/093650 A1 | 7/2009 |
| WO | WO-2009093650 A1 * | 7/2009 .............. A61P 27/02 |
| WO | 2010/098897 A1 | 9/2010 |
| WO | 2015/123631 A1 | 8/2015 |

OTHER PUBLICATIONS

International Search Report for International Application No. PCT/JP2018/000383 dated Mar. 6, 2018 (2 Sheets).
Office Action of corresponding Chinese Patent Application No. 201880002645.5 dated Mar. 1, 2021 (8 sheets).
Pan Weisan, et al.; Industrial Pharmacy; 3rd edition; China Medical Science and Technology Press; Aug. 2015; pp. 474 (cover sheet, 1 sheet, 2 sheets total).

* cited by examiner

Primary Examiner — Snigdha Maewall
(74) Attorney, Agent, or Firm — Kratz, Quintos & Hanson, LLP

(57) ABSTRACT

The drug-containing fat emulsion of the present invention, which comprises at least a slightly water soluble drug, an oil or fat, an emulsifier, and water as components, is characterized by having a content of the oil or fat of 2 to 120 mg/mL (excluding 2 mg/mL), having a weight ratio of the drug to the oil or fat (drug/(oil or fat)) of 0.001 to 20 (provided that the total content of the drug and the oil or fat is at most 125 mg/mL), having a content of lecithin as the emulsifier of 50 to 200 mg/mL (in which 50% by weight or less of the used lecithin is optionally replaced by an emulsifier other than lecithin), and having a turbidity of 0.5 or lower.

5 Claims, No Drawings

DRUG-CONTAINING FAT EMULSION AND METHOD FOR PRODUCING SAME

TECHNICAL FIELD

The present invention relates to a drug-containing fat emulsion that has transparency and is excellent in stability and safety, and a method for producing the same.

BACKGROUND ART

It is well known to persons skilled in the art that some of drug-containing fat emulsions, such as a steroid (dexamethasone palmitate)-containing fat emulsion and a prostaglandin ($PGE_1$)-containing fat emulsion, have been already placed on the market and commonly used. However, the emulsions are all milky white preparations in which a larger amount of oil or fat (the content is at least, for example, 10 mg/mL) is used as compared with the drug content and thus occurrence of deterioration or contamination, or change in formulation cannot be easily visually checked. It is therefore difficult to determine whether such an emulsion is acceptable. Further, some preparations are inferior in stability and thus are required to be stored in a cold place. The emulsions, therefore, have some restrictions. Accordingly, the present inventor proposes in Patent Document 1 a drug-containing fat emulsion that has transparency and is excellent in stability in which such restrictions are mitigated.

The drug-containing fat emulsion proposed by the present inventor in Patent Document 1 can be produced by making the oil or fat content at most 2 mg/mL, and has been appreciated as a drug-containing fat emulsion that has transparency and is excellent in stability. However, since the drug-containing fat emulsion has a small oil or fat content of at most 2 mg/mL, the amount of drug that can be carried by the fat emulsion is limited. Accordingly, there is a need for a drug-containing fat emulsion that contains a larger amount of oil or fat so that the fat emulsion can carry a larger amount of a drug while having transparency and being excellent in stability. In addition, in the production thereof, it is expected to use lecithin as an emulsifier among known emulsifiers for producing fat emulsions because of the high safety, in spite of its low emulsifying ability and its sometimes low handle-ability due to the high viscosity in high concentrations. The present inventor had made attempt to develop such a fat emulsion in order to meet the requirements, but had achieved no effective solution.

PRIOR ART DOCUMENTS

Patent Document

Patent Document 1: Japanese Patent No. 5340954

SUMMARY OF THE INVENTION

Problems that the Invention is to Solve

In view of the above situation, an object of the present invention is to provide a drug-containing fat emulsion that has transparency and is excellent in stability while having a higher oil or fat content so that the fat emulsion can carry a larger amount of a drug than heretofore known drug-containing fat emulsions having transparency and being excellent in stability, and that also has excellent in safety due to use of lecithin as an emulsifier, and a method for producing the drug-containing fat emulsion.

Means for Solving the Problems

As a result of intensive and extensive studies in view of the above situation, the present inventor has found that a drug-containing fat emulsion that has transparency and is excellent in stability while containing an oil or fat in an amount exceeding 2 mg/mL, and that also has excellent in safety due to use of lecithin as an emulsifier can be produced by making the content of the oil or fat, the weight ratio of the drug to the oil or fat, the total content of the drug and the oil or fat, and the content of lecithin as an emulsifier within suitable numerical ranges.

The present invention, which has been made based on the above findings, is directed to, as set forth in claim 1, a drug-containing fat emulsion comprising at least a slightly water soluble drug, an oil or fat, an emulsifier, and water as components, characterized by having a content of the oil or fat of 2 to 120 mg/mL (excluding 2 mg/mL), having a weight ratio of the drug to the oil or fat (drug/(oil or fat)) of 0.001 to 20 (provided that the total content of the drug and the oil or fat is at most 125 mg/mL), having a content of lecithin as the emulsifier of 50 to 200 mg/mL (in which 50% by weight or less of the used lecithin is optionally replaced by an emulsifier other than lecithin), and having a turbidity of 0.5 or lower.

The drug-containing fat emulsion set forth in claim 2 is characterized, in the drug-containing fat emulsion according to claim 1, in that fat particles have an average particle size of 1 to 200 nm.

The drug-containing fat emulsion set forth in claim 3 is characterized, in the drug-containing fat emulsion according to claim 1, by further containing at least one selected from propylene glycol, glycerol, macrogol, lactic acid, N,N-dimethylacetamide, polyvinyl alcohol, polyvinyl pyrrolidone, methyl cellulose, chondroitin sulfate or a salt thereof, hyaluronic acid or a salt thereof, and glycyrrhizinic acid or a salt thereof as a component.

The drug-containing fat emulsion set forth in claim 4 is characterized, in the drug-containing fat emulsion according to claim 1, by further containing a saccharide as a component.

The present invention is also directed to, as set forth in claim 5, a method for producing a drug-containing fat emulsion comprising at least a slightly water soluble drug, an oil or fat, an emulsifier, and water as components and having a turbidity of 0.5 or lower, characterized by comprising emulsifying the components to form an emulsion having a content of the oil or fat of 2 to 120 mg/mL (excluding 2 mg/mL), having a weight ratio of the drug to the oil or fat (drug/(oil or fat)) of 0.001 to 20 (provided that the total content of the drug and the oil or fat is at most 125 mg/mL), and having a content of lecithin as the emulsifier of 50 to 200 mg/mL (in which 50% by weight or less of the used lecithin is optionally replaced by an emulsifier other than lecithin).

The production method set forth in claim 6 is characterized, in the production method according to claim 5, in that the emulsification is performed at a pressure of 350 to 1500 bar.

Effect of the Invention

The present invention can provide a drug-containing fat emulsion that has transparency and is excellent in stability while having a higher oil or fat content so that the fat emulsion can carry a larger amount of a drug than heretofore known drug-containing fat emulsions having transparency and being excellent in stability, and that also has excellent in safety due to use of lecithin as an emulsifier, and a method for producing the drug-containing fat emulsion.

MODE FOR CARRYING OUT THE INVENTION

The present invention is directed to a drug-containing fat emulsion comprising at least a slightly water soluble drug, an oil or fat, an emulsifier, and water as components, characterized by having a content of the oil or fat of 2 to 120 mg/mL (excluding 2 mg/mL), having a weight ratio of the drug to the oil or fat (drug/(oil or fat)) of 0.001 to 20 (provided that the total content of the drug and the oil or fat is at most 125 mg/mL), having a content of lecithin as the emulsifier of 50 to 200 mg/mL (in which 50% by weight or less of the used lecithin is optionally replaced by an emulsifier other than lecithin), and having a turbidity of 0.5 or lower.

In the present invention, the slightly water soluble drugs include slightly water soluble drugs having a solubility, in terms of the solubility in water defined in General Notice of Japanese Pharmacopoeia, of "sparingly soluble" (the volume of solvent required for dissolving 1 g or 1 mL of solute is from 30 mL to less than 100 mL: the solute corresponds to the drug and the solvent corresponds to water) or lower solubility, and more suitably having a solubility of "slightly soluble" (the volume of solvent of the same is from 100 mL to less than 1000 mL) or lower solubility, and further suitably having a solubility of "very slightly soluble" (the volume of solvent of the same is from 1000 mL to less than 10000 mL) or lower solubility, and most suitably having a solubility of "practically insoluble" (the volume of solvent of the same is 10000 mL or over) or lower solubility. The drug may be slightly oil soluble while being slightly water soluble. The type of the drug is not particularly limited, and examples thereof include immunosuppressive drugs, such as ciclosporin and tacrolimus; antibiotics, such as erythromycin and clarithromycin; anti-inflammatory analgesics, such as indometacin, aspirin, ibuprofen, ketoprofen, diclofenac, ampiroxicam, and acetaminophen; synthetic adrenocortical hormone agents, such as dexamethasone palmitate, fluorometholone, betamethasone, and beclomethasone propionate; antimicrobial drugs, such as norfloxacin and levofloxacin; drugs for circulatory organ, such as tocopherol nicotinate; cerebral protective drugs, such as edaravone; drugs for liver disease, such as glycyrrhizinic acid-based compounds, for example, monoammoniumglycyrrhizinate; vitamin E drugs, such as tocopherol acetate; contrast agents, such as iodinated poppy seed oil fatty acid ethyl ester; antiviral drugs, such as vidarabine, aciclovir, and adefovir pivoxil; antineoplastic drugs, such as mitomycin, irinotecan, etoposide, paclitaxel, docetaxel, cabazitaxel, ubenimex, carboplatin, and cisplatin.

In the present invention, examples of the oils or fats include known oils or fats that can be used as an oil or fat, such as vegetable oils, for example, soybean oil, corn oil, coconut oil, safflower oil, perilla oil, olive oil, castor oil, and cotton seed oil, animal oils, for example, lanolin, egg yolk oils, fish oils, mineral oils, for example, liquid paraffin, medium-chain triglycerides, chemosynthesis triglycerides, and gelated hydrocarbons.

In the present invention, lecithin is used as the emulsifier. Specifically, lecithin may be a known lecithin that can be used as an emulsifier, such as egg yolk lecithin, soybean lecithin, hydrogenated egg yolk lecithin, or hydrogenated soybean lecithin. Incidentally, 50% by weight or less of the used lecithin may be replaced by another substance that can be used as an emulsifier (polysorbate, PEG-hydrogenated castor oil, polyoxyethylene castor oil, polyoxyethylene hydrogenated castor oil, and the like).

In the present invention, the reason why the content of the oil or fat is defined to 2 to 120 mg/mL (excluding 2 mg/mL) is that with a content of 2 mg/mL or less, the amount of a drug that can be carried by the fat emulsion is small, whereas with a content larger than of 120 mg/mL, emulsification is difficult due to the excessive oil or fat. The content of the oil or fat is preferably 10 to 110 mg/mL, more preferably 20 to 105 mg/mL, and further preferably 25 to 100 mg/mL. The reason why the weight ratio of the drug to the oil or fat (drug/(oil or fat)) is defined to 0.001 to 20 (provided that the total content of the drug and the oil or fat is at most 125 mg/mL) is that with a ratio less than 0.001, the oil or fat is excessive relative to the drug so that some useless oil or fat will be administered to patients, whereas with a ratio larger than 20, the drug is excessive relative to the oil or fat so that the stability of the drug is impaired and the drug is likely to aggregate or precipitate. The weight ratio of the drug to the oil or fat is preferably 0.01 to 10. The reason why the total content of the drug and the oil or fat is defined to at most 125 mg/mL is that with a total content larger than 125 mg/mL, emulsification for obtaining a fat emulsion having transparency is difficult. The total content of the drug and the oil or fat is preferably 3 to 120 mg/mL. The reason why the content of lecithin as the emulsifier is defined to 50 to 200 mg/mL is that with a content less than 50 mg/mL, emulsification is difficult due to excessive oil or fat relative to lecithin, whereas with a content larger than 200 mg/mL, emulsification is difficult due to increased viscosity of lecithin. As described above, 50% by weight or less of the used lecithin may be replaced by an emulsifier other than lecithin. In this case, the total content of lecithin and the emulsifier other than lecithin is 50 to 200 mg/mL so that the emulsifier is constituted of 50% by weight or more of lecithin and 50% by weight or less of the emulsifier other than lecithin. The content of lecithin is preferably 75 to 180 mg/mL, and more preferably 100 to 160 mg/mL. With a weight ratio of lecithin to the oil or fat (lecithin/(oil or fat)) of 1 to 300, a fat emulsion that has transparency and is excellent in stability is easily obtained. Incidentally, the content of the drug may be, for example, 0.1 to 50 mg/mL. When an oil or fat is used in an amount exceeding 2 mg/mL, a larger amount of a drug is carried by a fat emulsion, through dissolution in the oil or fat in cases of liposoluble drugs, or through coexistence with lecithin at an interface between water and the oil or fat in cases of non-liposoluble drugs.

The drug-containing fat emulsion of the present invention can be produced, with the content of the oil or fat, the weight ratio of the drug to the oil or fat, the total content of the drug and the oil or fat, and the content of lecithin as the emulsifier set within the above numerical ranges, by any procedure known per se, for example, by uniformly mixing a drug, an oil or fat, and lecithin to dissolve the components to thereby produce an oil phase, then, after adding water thereto or while adding water thereto, emulsifying the components using an ultrasonic homogenizer, or by vigorously agitating the components to prepare a coarse emulsion (for example, through agitation at a rotation number of 10000 to 15000 rpm for 5 to 30 minutes) and then emulsifying the coarse emulsion using a high pressure homogenizer, such as a Manton-Gaulin homogenizer. The particle size distribution of fat particles can be narrowed by controlling operation conditions of the homogenizer and emulsification time. Further, for narrowing the particle size distribution of fat particles, emulsification may be performed multiple times (for example, 3 to 50 times). It is notable that when emulsification is performed, with the content of the oil or fat, the weight ratio of the drug to the oil or fat, the total content of the drug and the oil or fat, and the content of lecithin set within the above numerical ranges, using an ultrasonic homogenizer or using a high pressure homogenizer at a pressure of, for example, 1500 bar or lower, and preferably 350 to 1000 bar, a drug-containing fat emulsion that has an average particle size of fat particles of 200 nm or less, suitably 180 nm or less, more suitably 120 nm or less, and further suitably 100 nm or less (the lower limit is, for example, 1 nm) and a turbidity of 0.5 or lower, suitably 0.4 or lower, more suitably 0.3 or lower, and further suitably 0.2 or lower, that is, a drug-containing fat emulsion that has transparency and is excellent in stability, is easily obtained.

Incidentally, propylene glycol, glycerol, macrogol, lactic acid, N,N-dimethylacetamide, polyvinyl alcohol, polyvinyl pyrrolidone, methyl cellulose, chondroitin sulfate or a salt thereof (such as sodium salt), hyaluronic acid or a salt thereof (such as sodium salt), or glycyrrhizinic acid or a salt thereof (such as sodium salt or ammonium salt) may further be used as a component of the drug-containing fat emulsion of the present invention in order to enhance the drug solubility, to enhance the stability of the fat emulsion or the drug, or to isotonize the fat emulsion, for example. The content of such a component is preferably 0.02 to 300 mg/mL, and more preferably 0.2 to 100 mg/mL. With a content less than 0.02 mg/mL, the effect is hardly exhibited, whereas with a content larger than 300 mg/mL, emulsification is difficult due to increased viscosity or the fat emulsion is unstable due to acidification thereof.

In addition, a higher fatty acid, such as oleic acid, stearic acid, linoleic acid, linolenic acid, palmitic acid, palmitoleic acid, or myristic acid, may further be used as a component of the drug-containing fat emulsion of the present invention in order to stabilize the fat emulsion. The content of such a higher fatty acid is preferably 0.001 to 10 mg/mL, and more preferably 0.01 to 5 mg/mL. With a content less than 0.001 mg/mL, the effect is hardly exhibited, whereas with a content larger than 10 mg/mL, there is a risk to degrade the drug.

In addition, when a saccharide is further used as a component of the drug-containing fat emulsion of the present invention, appearance of precipitated floaters which may appear in some cases can be effectively suppressed. Suitable examples of saccharides include monosaccharides, such as inositol, glucose, sorbitol, fructose, and mannitol, disaccharides, such as trehalose, lactose, sucrose, and maltose, dextrin, cyclodextrin, dextran, and xylitol. The content of such a saccharide is preferably 10 to 600 mg/mL.

In addition, a pH modifier or an osmotic pressure modifier known per se may further be used as a component of the drug-containing fat emulsion of the present invention in order to modify pH (for example, 3.5 to 9) or to modify the osmotic pressure so as to stabilize the fat emulsion. Incidentally, a preservative, an antioxidant, or the like may of course be used as a component as required. Also, the drug-containing fat emulsion of the present invention is not discouraged from containing a water soluble drug as a component.

For the drug-containing fat emulsion of the present invention, filtration sterilization may be easily performed by, for example, setting the average particle size to 200 nm or less, and high pressure steam sterilization may be performed. High pressure steam sterilization may be performed at common conditions (for example, at 120 to 122° C. for 10 to 15 minutes) after filling the drug-containing fat emulsion of the present invention in a glass ample or a synthetic resin vessel.

The drug-containing fat emulsion of the present invention is excellent in stability, and thus can be stored at room temperature (for example, 5 to 30° C.) (provided that this does not apply to the case where the drug itself is very unstable). In addition, the fact that it has transparency makes it easy to visually check occurrence of deterioration or contamination, and change in formulation, and provides a sense of safety to a patient whom the fat emulsion is administered. These effects particularly effectively function in cases where the drug-containing fat emulsion of the present invention is used as an injection, an eye drop, a nasal drop, an ear drop, or an inhalant.

EXAMPLES

Hereinafter, the present invention is explained in detail with reference to examples, but the present invention should not be construed to be limited to the following description.

Example 1: Dexamethasone Palmitate-Containing Fat Emulsion (1)

After 40 mg of dexamethasone palmitate and 500 mg of a commercially available purified soybean oil were dissolved with stirring under heat (60° C.), 4 g of a purified egg yolk lecithin (PC-98N: manufactured by Kewpie Corporation, the same applies hereinafter) and 260 mg of propylene glycol were added and uniformly mixed therein to prepare an oil phase. While adding 14 mL of purified water portionwise to the oil phase, the mixture was emulsified with an ultrasonic homogenizer (manufactured by SMT Corporation, the same applies hereinafter) for 30 minutes. After emulsification, the volume was made up to 20 mL with purified water, and then filtration sterilization was performed with a cellulose acetate membrane (CA membrane, the same applies hereinafter) of 0.22 μmϕ, thereby obtaining a target transparent dexamethasone palmitate-containing fat emulsion. The physical properties are shown in Table 1.

Example 2: Dexamethasone Palmitate-Containing Fat Emulsion (2)

After 20 mg of dexamethasone palmitate and 800 mg of a commercially available purified soybean oil were dissolved with stirring under heat (60° C.), 4 g of a purified egg yolk lecithin (PC-98N) and 200 mg of glycerol were added and uniformly mixed therein to prepare an oil phase. While adding 14 mL of purified water portionwise to the oil phase, the mixture was emulsified with an ultrasonic homogenizer for 30 minutes. After emulsification, the volume was made up to 20 mL with purified water, and then filtration sterilization was performed with a 0.22 μmϕ CA membrane, thereby obtaining a target transparent dexamethasone palmitate-containing fat emulsion. The physical properties are shown in Table 1.

Example 3: Tacrolimus-containing Fat Emulsion (1)

After 100 mg of tacrolimus, 500 mg of a commercially available purified soybean oil, and 500 mg of a commercially available medium-chain triglyceride were dissolved with stirring under heat (60° C.), 2.6 g of a purified egg yolk lecithin (PL-100M: manufactured by Kewpie Corporation, the same applies hereinafter) and 200 mg of glycerol were added and uniformly mixed therein to prepare an oil phase. While adding 15 mL of purified water portionwise to the oil phase, the mixture was emulsified with an ultrasonic homogenizer for 30 minutes. After emulsification, the volume was made up to 20 mL with purified water, and then filtration sterilization was performed with a 0.22 μmϕ CA membrane, thereby obtaining a target transparent tacrolimus-containing fat emulsion. The physical properties are shown in Table 1 (pH: 5.6).

Example 4: Iodinated Poppy Seed Oil Fatty Acid Ethyl Ester-containing Fat Emulsion While 400 mg of iodinated poppy seed oil fatty acid ethyl ester (since iodinated poppy seed oil fatty acid ethyl ester is a drug that is also an oil or fat, the amount was taken as the total amount of the drug and the oil or fat) was heated (60° C.), 2.6 g of a purified egg yolk lecithin (PL-100M) and 400 mg of glycerol were added and uniformly mixed therein to prepare an oil phase. While adding 16 mL of purified water portionwise to the oil phase, the mixture was emulsified with an ultrasonic homogenizer for 30 minutes. After emulsification, the volume was made up to 20 mL with purified water, and then filtration sterilization was performed with a 0.22 μmϕ CA membrane, thereby obtaining a target transparent iodinated poppy seed oil fatty acid ethyl ester-containing fat emulsion. The physical properties are shown in Table 1 (pH: 6.3).

Example 5: Dexamethasone Palmitate-containing Fat Emulsion (3)

After 20 mg of dexamethasone palmitate and 600 mg of a commercially available purified soybean oil were dissolved with stirring under heat (60° C.), 1.6 g of a purified egg yolk lecithin (PL-100M), 2.4 g of a purified egg yolk lecithin (PC-98N), and 200 mg of glycerol were added and uniformly mixed therein to prepare an oil phase. While adding 15 mL of purified water portionwise to the oil phase, the mixture was emulsified with an ultrasonic homogenizer for 30 minutes. After emulsification, the volume was made up to 20 mL with purified water, and then filtration sterilization was performed with a 0.22 μmϕ CA membrane, thereby obtaining a target transparent dexamethasone palmitate-containing fat emulsion. The physical properties are shown in Table 1.

Example 6: Dexamethasone Palmitate-containing Fat Emulsion (4)

After 14 mg of dexamethasone palmitate and 2 g of a commercially available medium-chain triglyceride were dissolved with stirring under heat (60° C.), 2.66 g of a purified egg yolk lecithin (PL-100M) and 260 mg of glycerol were added and uniformly mixed therein to prepare an oil phase. While adding 15 mL of purified water portionwise to the oil phase, the mixture was emulsified with an ultrasonic homogenizer for 30 minutes. After emulsification, the volume was made up to 20 mL with purified water, and then filtration sterilization was performed with a 0.22 μmϕ CA membrane, thereby obtaining a target transparent dexamethasone palmitate-containing fat emulsion. The physical properties are shown in Table 1.

Example 7: Dexamethasone Palmitate-containing Fat Emulsion (5)

After 40 mg of dexamethasone palmitate and 2.4 g of a commercially available medium-chain triglyceride were dissolved with stirring under heat (60° C.), 3 g of a purified egg yolk lecithin (PL-100M) was added and uniformly mixed therein to prepare an oil phase. While adding 14 mL of purified water portionwise to the oil phase, the mixture was emulsified with an ultrasonic homogenizer for 30 minutes. After emulsification, the volume was made up to 20 mL with purified water, and then filtration sterilization was performed with a 0.22 μmϕ CA membrane, thereby obtaining a target transparent dexamethasone palmitate-containing fat emulsion. The physical properties are shown in Table 1.

Example 8: Dexamethasone Palmitate-containing Fat Emulsion (6)

After 80 mg of dexamethasone palmitate and 2 g of a commercially available medium-chain triglyceride were dissolved with stirring under heat (60° C.), 1.8 g of a purified egg yolk lecithin (PL-100M) and 400 mg of glycerol were added and uniformly mixed therein to prepare an oil phase. While adding 15 mL of purified water portionwise to the oil phase, the mixture was emulsified with an ultrasonic homogenizer for 30 minutes. After emulsification, the volume was made up to 20 mL with purified water, and then filtration sterilization was performed with a 0.22 μmϕ CA membrane, thereby obtaining a target transparent dexamethasone palmitate-containing fat emulsion. The physical properties are shown in Table 1.

Example 9: Ciclosporin-containing Fat Emulsion

After 40 mg of ciclosporin and 500 mg of a commercially available medium-chain triglyceride were dissolved with stirring under heat (60° C.), 1 g of a purified egg yolk lecithin (PL-100M) and 460 mg of propylene glycol were added and uniformly mixed therein to prepare an oil phase. While adding 18 mL of purified water portionwise to the oil phase, the mixture was emulsified with an ultrasonic homogenizer for 30 minutes. After emulsification, the volume was made up to 20 mL with purified water, and then filtration sterilization was performed with a 0.22 μmϕ CA membrane, thereby obtaining a target transparent ciclosporin-containing fat emulsion. The physical properties are shown in Table 1 (pH: 5.3).

Example 10: Tocopherol Acetate-containing Fat Emulsion

After 500 mg of tocopherol acetate and 500 mg of a commercially available medium-chain triglyceride were dissolved with stirring under heat (60° C.), 2.6 g of a purified egg yolk lecithin (PL-100M) and 400 mg of propylene glycol were added and uniformly mixed therein to prepare an oil phase. While adding 16 mL of purified water portionwise to the oil phase, the mixture was emulsified with an ultrasonic homogenizer for 30 minutes. After emulsification, the volume was made up to 20 mL with purified water, and then filtration sterilization was performed with a 0.22 μmϕ CA membrane, thereby obtaining a target transparent tocopherol acetate-containing fat emulsion. The physical properties are shown in Table 1 (pH: 6.8).

Example 11: Tacrolimus-containing Fat Emulsion (2)

After 40 mg of tacrolimus and 1 g of a commercially available medium-chain triglyceride were dissolved with stirring under heat (60° C.), 4 g of a purified egg yolk lecithin (PC-98N) and 200 mg of glycerol were added and uniformly mixed therein to prepare an oil phase. While adding 14 mL of purified water portionwise to the oil phase, the mixture was emulsified with an ultrasonic homogenizer for 30 minutes. After emulsification, the volume was made up to 20 mL with purified water, and then filtration sterilization was performed with a 0.22 µmϕ CA membrane, thereby obtaining a target transparent tacrolimus-containing fat emulsion. The physical properties are shown in Table 1.

Example 12: Tacrolimus-containing Fat Emulsion (3)

After 40 mg of tacrolimus and 2 g of a commercially available medium-chain triglyceride were dissolved with stirring under heat (60° C.), 4 g of a purified egg yolk lecithin (PC-98N) and 200 mg of glycerol were added and uniformly mixed therein to prepare an oil phase. While adding 13 mL of purified water portionwise to the oil phase, the mixture was emulsified with an ultrasonic homogenizer for 30 minutes. After emulsification, the volume was made up to 20 mL with purified water, and then filtration sterilization was performed with a 0.22 µmϕ CA membrane, thereby obtaining a target transparent tacrolimus-containing fat emulsion. The physical properties are shown in Table 1.

Example 13: Dexamethasone Palmitate-containing Fat Emulsion (7)

After 80 mg of dexamethasone palmitate and 2 g of a commercially available medium-chain triglyceride were dissolved with stirring under heat (60° C.), 1.8 g of a purified egg yolk lecithin (PL-100M) and 400 mg of glycerol were added and uniformly mixed therein to prepare an oil phase. While adding 15 mL of purified water portionwise to the oil phase, the mixture was emulsified with an ultrasonic homogenizer for 30 minutes. After emulsification, the volume was made up to 20 mL with purified water, glucose was added at 100 mg/mL to dissolve in the emulsion by mixing with the ultrasonic homogenizer for 5 minutes, and then filtration sterilization was performed with a 0.22 µmϕ CA membrane, thereby obtaining a target transparent dexamethasone palmitate-containing fat emulsion. The physical properties are shown in Table 1.

Example 14: Tacrolimus-containing Fat Emulsion (4)

After 40 mg of tacrolimus and 2 g of a commercially available medium-chain triglyceride were dissolved with stirring under heat (60° C.), 4 g of a purified egg yolk lecithin (PC-98N) and 200 mg of glycerol were added and uniformly mixed therein to prepare an oil phase. While adding 13 mL of purified water portionwise to the oil phase, the mixture was emulsified with an ultrasonic homogenizer for 30 minutes. After emulsification, the volume was made up to 20 mL with purified water, trehalose was added at 100 mg/mL to dissolve in the emulsion by mixing with the ultrasonic homogenizer for 5 minutes, and then filtration sterilization was performed with a 0.22 µmϕ CA membrane, thereby obtaining a target transparent tacrolimus-containing fat emulsion. The physical properties are shown in Table 1.

Example 15: Dexamethasone Palmitate-containing Fat Emulsion (8)

750 mg of dexamethasone palmitate, 1.5 g of a commercially available purified soybean oil, 18 g of a purified egg yolk lecithin (PL-100M), and 3 g of glycerol were uniformly mixed using a general-purpose mixer under heat (60° C.) to dissolve the components to thereby prepare an oil phase. Under stirring using a high flex disperser (manufactured by SMT Corporation, the same applies hereinafter), 120 mL of purified water was added portionwise to the oil phase, and after completion of the addition, the mixture was coarsely emulsified at 12000 rpm for 10 minutes. After purified water was further added to make the liquid volume up to 150 mL, the resultant was finely emulsified using a high pressure homogenizer (LAB2000: manufactured by SMT Corporation, the same applies hereinafter). The emulsification pressure was 1450 bar, and the emulsification number was 20 times (circulation emulsification). After emulsification, 1N aqueous hydrochloric acid solution was added as a pH modifier to adjust the pH to 7.0, and then filtration sterilization was performed with a 0.22 µmϕ CA membrane, thereby obtaining a target transparent dexamethasone palmitate-containing fat emulsion. The physical properties are shown in Table 1.

Example 16: Dexamethasone Palmitate-containing Fat Emulsion (9)

600 mg of dexamethasone palmitate, 3.75 g of a commercially available medium-chain triglyceride, 19.5 g of a purified egg yolk lecithin (PL-100M), and 3 g of propylene glycol were uniformly mixed using a general-purpose mixer under heat (60° C.) to dissolve the components to thereby prepare an oil phase. Under stirring using a high flex disperser, 120 mL of purified water was added portionwise to the oil phase, and after completion of the addition, the mixture was coarsely emulsified at 12000 rpm for 10 minutes. After purified water was further added to make the liquid volume up to 150 mL, the resultant was finely emulsified using a high pressure homogenizer. The emulsification pressure was 1450 bar, and the emulsification number was 20 times (circulation emulsification). After emulsification, 1N aqueous hydrochloric acid solution was added as a pH modifier to adjust the pH to 7.0, and then filtration sterilization was performed with a 0.22 µmϕ CA membrane, thereby obtaining a target transparent dexamethasone palmitate-containing fat emulsion. The physical properties are shown in Table 1.

Example 17: Dexamethasone Palmitate-containing Fat Emulsion (10)

After 100 mg of dexamethasone palmitate and 400 mg of a commercially available purified soybean oil were dissolved using a compact ultrasonic washer (manufactured by AS ONE Corporation, the same applies hereinafter) under heat (60° C.), 1 g of a purified egg yolk lecithin (PC-98N), 1 g of polysorbate (manufactured by NOF CORPORATION, the same applies hereinafter), and 100 mg of glycerol were added and uniformly mixed therein to prepare an oil phase. While adding 7 mL of purified water portionwise to the oil phase, the mixture was emulsified with an ultrasonic homogenizer for 20 minutes. After emulsification, the volume was made up to 10 mL with purified water, and then filtration sterilization was performed with a 0.22 μmϕ CA membrane, thereby obtaining a target transparent dexamethasone palmitate-containing fat emulsion. The physical properties are shown in Table 1.

Example 18: Indometacin-containing Fat Emulsion

After 100 mg of indometacin and 1 g of a commercially available medium-chain triglyceride were dissolved using a compact ultrasonic washer under heat (60° C.), 1 g of a purified egg yolk lecithin (PC-98N), 1 g of polysorbate 80, and 900 mg of propylene glycol were added and uniformly mixed therein to prepare an oil phase. While adding 6 mL of purified water portionwise to the oil phase, the mixture was emulsified with an ultrasonic homogenizer for 20 minutes. After emulsification, the volume was made up to 10 mL with purified water, and then filtration sterilization was performed with a 0.22 μmϕ CA membrane, thereby obtaining a target transparent indometacin-containing fat emulsion. The physical properties are shown in Table 1.

Example 19: Dexamethasone Palmitate-containing Fat Emulsion (11)

After 40 mg of dexamethasone palmitate and 1 g of a commercially available medium-chain triglyceride were dissolved using a compact ultrasonic washer under heat (70° C.), 450 mg of a purified egg yolk lecithin (PL-100M), 450 mg of polysorbate 80, and 200 mg of glycerol were added and uniformly mixed therein to prepare an oil phase. While adding 7.5 mL of purified water portionwise to the oil phase, the mixture was emulsified with an ultrasonic homogenizer for 30 minutes. After emulsification, the volume was made up to 10 mL with purified water, and then filtration with a 0.45 μmϕ CA membrane and filtration sterilization with a 0.22 μmϕ CA membrane were sequentially performed, thereby obtaining a target transparent dexamethasone palmitate-containing fat emulsion. The physical properties are shown in Table 1.

Example 20: Dexamethasone Palmitate-containing Fat Emulsion (12)

After 40 mg of dexamethasone palmitate and 1 g of a commercially available medium-chain triglyceride were dissolved using a compact ultrasonic washer under heat (70° C.), 450 mg of a purified egg yolk lecithin (PL-100M), 450 mg of polyoxyethylene castor oil (UNIOX C-35: manufactured by NOF CORPORATION, the same applies hereinafter), and 200 mg of glycerol were added and uniformly mixed therein to prepare an oil phase. While adding 7.5 mL of purified water portionwise to the oil phase, the mixture was emulsified with an ultrasonic homogenizer for 30 minutes. After emulsification, the volume was made up to 10 mL with purified water, and then filtration with a 0.45 μmϕ CA membrane and filtration sterilization with a 0.22 μmϕ CA membrane were sequentially performed, thereby obtaining a target transparent dexamethasone palmitate-containing fat emulsion. The physical properties are shown in Table 1.

Example 21: Dexamethasone Palmitate-containing Fat Emulsion (13)

After 40 mg of dexamethasone palmitate and 1 g of a commercially available medium-chain triglyceride were dissolved using a compact ultrasonic washer under heat (70° C.), 1 g of a purified egg yolk lecithin (PL-100M), 500 mg of polyoxyethylene castor oil, and 200 mg of glycerol were added and uniformly mixed therein to prepare an oil phase. While adding 7 mL of purified water portionwise to the oil phase, the mixture was emulsified with an ultrasonic homogenizer for 30 minutes. After emulsification, the volume was made up to 10 mL with purified water, and then filtration with a 0.45 μmϕ CA membrane and filtration sterilization with a 0.22 μmϕ CA membrane were sequentially performed, thereby obtaining a target transparent dexamethasone palmitate-containing fat emulsion. The physical properties are shown in Table 1.

Example 22: Dexamethasone Palmitate-containing Fat Emulsion (14)

After 40 mg of dexamethasone palmitate and 1 g of a commercially available medium-chain triglyceride were dissolved using a compact ultrasonic washer under heat (70° C.), 600 mg of a purified egg yolk lecithin (PL-100M), 600 mg of polysorbate 80, and 200 mg of glycerol were added and uniformly mixed therein to prepare an oil phase. While adding 7.5 mL of purified water portionwise to the oil phase, the mixture was emulsified with an ultrasonic homogenizer for 30 minutes. After emulsification, the volume was made up to 10 mL with purified water, and then filtration with a 0.45 μmϕ CA membrane and filtration sterilization with a 0.22 μmϕ CA membrane were sequentially performed, thereby obtaining a target transparent dexamethasone palmitate-containing fat emulsion. The physical properties are shown in Table 1.

Example 23: Dexamethasone Palmitate-containing Fat Emulsion (15)

After 40 mg of dexamethasone palmitate and 200 mg of a commercially available medium-chain triglyceride were dissolved using a compact ultrasonic washer under heat (70° C.), 1 g of a purified egg yolk lecithin (PL-100M), 500 mg of polysorbate 80, and 200 mg of glycerol were added and uniformly mixed therein to prepare an oil phase. While adding 8 mL of purified water portionwise to the oil phase, the mixture was emulsified with an ultrasonic homogenizer for 30 minutes. After emulsification, the volume was made up to 10 mL with purified water, and then filtration with a 0.45 μmϕ CA membrane and filtration sterilization with a 0.22 μmϕ CA membrane were sequentially performed, thereby obtaining a target transparent dexamethasone palmitate-containing fat emulsion. The physical properties are shown in Table 1.

Comparative Example 1

After 200 mg of ciclosporin and 2.4 g of a commercially available medium-chain triglyceride were dissolved with stirring under heat (60° C.), 3.6 g of a purified egg yolk lecithin (PL-100M) was added and uniformly mixed therein to prepare an oil phase. While adding 13 mL of purified water portionwise to the oil phase, the mixture was emulsified with an ultrasonic homogenizer for 30 minutes. However, the resulting emulsion was immediately solidified.

Comparative Example 2

After 400 mg of iodinated poppy seed oil fatty acid ethyl ester and 2.4 g of a commercially available medium-chain triglyceride were dissolved with stirring under heat (60° C.), 3.6 g of a purified egg yolk lecithin (PL-100M) was added and uniformly mixed therein to prepare an oil phase. While adding 13 mL of purified water portionwise to the oil phase, the mixture was emulsified with an ultrasonic homogenizer for 30 minutes. After emulsification, the volume was made up to 20 mL with purified water, and then filtration sterilization was performed with a 0.22 μmφ CA membrane, thereby obtaining an iodinated poppy seed oil fatty acid ethyl ester-containing fat emulsion. However, the fat emulsion was white.

Comparative Example 3

After 100 mg of dexamethasone palmitate and 2 g of a commercially available purified soybean oil were dissolved with stirring under heat (60° C.), 4.4 g of a purified egg yolk lecithin (PL-100M) and 440 mg of glycerol were added and uniformly mixed therein to prepare an oil phase. While adding 13 mL of purified water portionwise to the oil phase, the mixture was emulsified with an ultrasonic homogenizer for 30 minutes. After emulsification, the volume was made up to 20 mL with purified water, and then filtration sterilization was performed with a 0.22 μmφ CA membrane, thereby obtaining a dexamethasone palmitate-containing fat emulsion. However, the fat emulsion was clouded.

TABLE 1

| | Drug | Solubility in water (expression in Japanese Pharmacopoeia) | Concentration of drug (mg/mL) | Concentration of oil or fat (mg/mL) | Type and concentration (mg/mL) of emulsifier | | Turbidity | Average particle size (nm) |
|---|---|---|---|---|---|---|---|---|
| Ex. 1 | Dexamethasone palmitate | Practically insoluble | 2 | 25 | Egg yolk lecithin | 200 | 0.204 | 52 |
| Ex. 2 | Dexamethasone palmitate | Practically insoluble | 1 | 40 | Egg yolk lecithin | 200 | 0.396 | 60 |
| Ex. 3 | Tacrolimus | Practically insoluble | 5 | 50 | Egg yolk lecithin | 130 | 0.271 | 55 |
| Ex. 4 | Iodinated poppy seed oil fatty acid ethyl ester | Insoluble | 20 (Total concentration of drug and oil or fat) | | Egg yolk lecithin | 130 | 0.309 | 54 |
| Ex. 5 | Dexamethasone palmitate | Practically insoluble | 1 | 30 | Egg yolk lecithin mixture | 200 | 0.197 | 50 |
| Ex. 6 | Dexamethasone palmitate | Practically insoluble | 0.7 | 100 | Egg yolk lecithin | 133 | 0.324 | 59 |
| Ex. 7 | Dexamethasone palmitate | Practically insoluble | 2 | 120 | Egg yolk lecithin | 150 | 0.436 | 61 |
| Ex. 8 | Dexamethasone palmitate | Practically insoluble | 4 | 100 | Egg yolk lecithin | 90 | 0.469 | 62 |
| Ex. 9 | Ciclosporin | Practically insoluble | 2 | 25 | Egg yolk lecithin | 50 | 0.143 | 37 |
| Ex. 10 | Tocopherol acetate | Practically insoluble | 25 | 25 | Egg yolk lecithin | 130 | 0.337 | 58 |
| Ex. 11 | Tacrolimus | Practically insoluble | 2 | 50 | Egg yolk lecithin | 200 | 0.188 | 39 |
| Ex. 12 | Tacrolimus | Practically insoluble | 2 | 100 | Egg yolk lecithin | 200 | 0.416 | 57 |
| Ex. 13 | Dexamethasone palmitate | Practically insoluble | 4 | 100 | Egg yolk lecithin | 90 | 0.428 | 61 |
| Ex. 14 | Tacrolimus | Practically insoluble | 2 | 100 | Egg yolk lecithin | 200 | 0.391 | 56 |
| Ex. 15 | Dexamethasone palmitate | Practically insoluble | 5 | 10 | Egg yolk lecithin | 120 | 0.168 | 40 |
| Ex. 16 | Dexamethasone palmitate | Practically insoluble | 4 | 25 | Egg yolk lecithin | 130 | 0.232 | 42 |
| Ex. 17 | Dexamethasone palmitate | Practically insoluble | 10 | 40 | Egg yolk lecithin polysorbate | 100 100 | 0.032 | 37 |
| Ex. 18 | Indometacin | Practically insoluble | 10 | 100 | Egg yolk lecithin polysorbate | 100 100 | 0.026 | 38 |
| Ex. 19 | Dexamethasone palmitate | Practically insoluble | 4 | 100 | Egg yolk lecithin polysorbate | 45 45 | 0.315 | 49 |
| Ex. 20 | Dexamethasone palmitate | Practically insoluble | 4 | 100 | Egg yolk lecithin polyoxyethylene castor oil | 45 45 | 0.273 | 51 |
| Ex. 21 | Dexamethasone palmitate | Practically insoluble | 4 | 100 | Egg yolk lecithin polyoxyethylene castor oil | 100 50 | 0.221 | 55 |
| Ex. 22 | Dexamethasone palmitate | Practically insoluble | 4 | 100 | Egg yolk lecithin polysorbate | 60 60 | 0.152 | 34 |
| Ex. 23 | Dexamethasone palmitate | Practically insoluble | 4 | 20 | Egg yolk lecithin polysorbate | 100 50 | 0.036 | 41 |
| Comp. Ex. 1 | Ciclosporin | Practically insoluble | 10 | 120 | Egg yolk lecithin | 180 | not measurable | not measured |
| Comp. Ex. 2 | Iodinated poppy seed oil fatty acid ethyl ester | Insoluble | 140 (Total concentration of drug and oil or fat) | | Egg yolk lecithin | 180 | 1.813 | 125 |
| Comp. Ex. 3 | Dexamethasone palmitate | Practically insoluble | 5 | 100 | Egg yolk lecithin | 220 | 0.725 | 70 |

Incidentally, the turbidity was measured using an ultraviolet spectrophotometer (UV1800: manufactured by Shimadzu Corporation) at a wavelength of λ=620 nm with a sample placed in a measurement cell having a width of 1 cm (water was used as blank). Abs (absorbance) of 0.5 or lower, which is a range of transparent to translucent at which a sample looks transparent, and occurrence of deterioration, such as aggregation or sedimentation, or contamination, or change in formulation can be easily visually checked, was taken as a boundary of acceptable turbidity. The average particle size was measured using a particle size analyzer (Zetasizer Nano ZS: manufactured by Malvern Panalytical Ltd.) which is based on the photon correlation method.

As is clear from Table 1, all the drug-containing fat emulsions of Example 1 to 23 have an average particle size of 100 nm or less, showing a quite high transparency, and even after storage at room temperature for one month, there is no recognized change that will interfere with a practical use, showing excellent storage stability (through visual observation for occurrence of phase separation, sedimentation, precipitation, phase change, and the like). On the other hand, a target transparent drug-containing fat emulsion was not obtained in Comparative Example 1 and Comparative Example 2, and this was supposedly attributable to the excessive total content of the drug and the oil or fat. A target transparent drug-containing fat emulsion was not obtained also in Comparative Example 3, and this was supposedly attributable to the excessive content of lecithin.

INDUSTRIAL APPLICABILITY

The present invention has an industrial applicability in the point of capability of providing a drug-containing fat emulsion that has transparency and is excellent in stability while having a higher oil or fat content so that the fat emulsion can carry a larger amount of a drug than heretofore known drug-containing fat emulsions having transparency and being excellent in stability, and that also has excellent in safety due to use of lecithin as an emulsifier, and a method for producing the drug-containing fat emulsion.

The invention claimed is:

1. A drug-containing fat emulsion comprising as components at least:
   a slightly water soluble drug,
   an oil or fat,
   an emulsifier, and water,
   wherein:
   the content of the oil or fat in the emulsion is in the range of 25 to 120 mg/mL,
   the weight ratio of the drug to the oil or fat is in the range of 0.001 to 20,
   the total content of the drug and the oil or fat is at most 125 mg/mL,
   50% or more by weight of the emulsifier is lecithin,
   the weight ratio of the emulsifier to the oil or fat is in the range of 1 to 300,
   the content of the emulsifier in the emulsion is in the range of 50 to 200 mg/mL,
   the turbidity of the emulsion is 0.5 or lower,
   wherein the average particle size of fat particles in the emulsion is 100 nm or less, and
   wherein the drug-containing fat emulsion after storage for one month at room temperature shows no visual occurrence of phase separation, sedimentation, precipitation or phase change.

2. The drug-containing fat emulsion according to claim 1, further containing at least one selected from propylene glycol, glycerol, macrogol, lactic acid, N,N-dimethylacetamide, polyvinyl alcohol, polyvinyl pyrrolidone, methyl cellulose, chondroitin sulfate or a salt thereof, hyaluronic acid or a salt thereof, and glycyrrhizinic acid or a salt thereof as a component.

3. The drug-containing fat emulsion according to claim 1, further containing a saccharide as a component.

4. A method for producing the drug-containing fat emulsion according to claim 1, comprising emulsifying the components to form an emulsion having a content of the oil or fat of 25 to 120 mg/mL, having a weight ratio of the drug to the oil or fat of 0.001 to 20, wherein the total content of the drug and the oil or fat is at most 125 mg/mL, 50% or more by weight of the emulsifier is lecithin, the weight ratio of the emulsifier to the oil or fat is in a range of 1 to 300, and the content of the emulsifier in the emulsion is in the range of 50 to 200 mg/mL.

5. The production method according to claim 4, wherein the emulsification is performed at a pressure of 350 to 1500 bar.

* * * * *